United States Patent
Jang et al.

(10) Patent No.: US 10,451,635 B2
(45) Date of Patent: Oct. 22, 2019

(54) BEEF-SPECIFIC AGE DETERMINATION MARKER CONTAINING THE P21 PROTEIN

(71) Applicant: Korea Basic Science Institute, Daejeon (KR)

(72) Inventors: Ik Soon Jang, Seoul (KR); Jong Soon Choi, Daejeon (KR); Joseph Kwon, Jeonju-si (KR); Dong-Gi Lee, Daejeon (KR); Kyeong Eun Yang, Gwangju (KR)

(73) Assignee: KOREA BASIC SCIENCE INSTITUTE, Daejeon (KR)

( * ) Notice: Subject to any disclaimer, the term of this patent is extended or adjusted under 35 U.S.C. 154(b) by 408 days.

(21) Appl. No.: 15/339,773

(22) Filed: Oct. 31, 2016

(65) Prior Publication Data

US 2017/0067911 A1     Mar. 9, 2017

Related U.S. Application Data

(63) Continuation-in-part of application No. 13/519,769, filed as application No. PCT/KR2010/009307 on Dec. 24, 2010.

(30) Foreign Application Priority Data

Dec. 30, 2009 (KR) .................. 10-2009-0134212

(51) Int. Cl.
*G01N 33/68* (2006.01)
*C07K 16/18* (2006.01)

(52) U.S. Cl.
CPC ......... *G01N 33/6887* (2013.01); *C07K 16/18* (2013.01); *G01N 2333/82* (2013.01)

(58) Field of Classification Search
None
See application file for complete search history.

(56) References Cited

U.S. PATENT DOCUMENTS

| 2005/0239116 A1 | 10/2005 | Willey |
| 2008/0051328 A1 | 2/2008 | Sharma et al. |
| 2012/0329057 A1 | 12/2012 | Jang et al. |

FOREIGN PATENT DOCUMENTS

| KR | 10-832348 B1 | 5/2008 |
| KR | 10-2009-0041273 A | 4/2009 |
| KR | 10-2009-0043777 A | 5/2009 |
| KR | 10-2009-0088225 A | 8/2009 |

OTHER PUBLICATIONS

Park et al; Age-dependent changes of p57Kip2 and p21Cip1/Waf1 expression in skeletal muscle and lung of mice; Biochimica et Biophysica Acta, 1520 (2001); pp. 163-168.
Bond et al; Biphasic effect of p21cip1 on smooth muscle cell proliferation: Role of PI 3-kinase and Skp2-mediated degradation, Cardiovascular Research, 69 (2006), pp. 198-206.
"A Focus on Bovine Spongiform Encephalopathy" Pathogens and Contaminants; Food Safety Research Information Office; Nov. 2007; Archived from the original on Mar. 3, 2008; Retrieved on Dec. 11, 2013; 9 pages.
English translation and Korean language International Search Report dated Sep. 26, 2011, issued in PCT Application No. PCT/KR2010/009307, filed Dec. 24, 2010; 4 pages.

*Primary Examiner* — Christine Foster
*Assistant Examiner* — Ellen J Marcsisin
(74) *Attorney, Agent, or Firm* — Lucas & Mercanti, LLP

(57) ABSTRACT

The present invention relates to a beef-specific age determination marker containing the p21 protein, to an antibody specifically bound to bovine p21 protein, to a beef-specific age determination kit containing the antibody which is specifically bound to the bovine p21 protein, and to a method which involves detecting the bovine p21 protein through an antigen-antibody binding reaction using the antibody which is specifically bound to the bovine p21 protein serving as a beef-specific age determination marker in the muscle tissue of beef, so as to determine the age of the beef. According to the present invention, the p21 protein is significantly greatly expressed in the muscle tissue of beef, the age of which is lower than 30 months, and is hardly expressed in the muscle tissue of beef, the age of which is greater than 30 months, and thus can be valuably used as a beef-specific age determination marker.

4 Claims, 10 Drawing Sheets

Specification includes a Sequence Listing.

Bovine

MSELSRDAHQ IPRSSKACRC LFGPVDSEQL RQDCDALMAS CVQEARERWN
FDFVTETPLE GDFAWERVRG LGLPKLYLPV GPRDDLGGGK RPSPSSALLQ
GTSQEDHLDL SLSCTLVTRS PERPEGTPGG PGPSQGRKRR QTSMTDFYHS
KRRLICSKRK P (SEQ ID NO: 1)

26-37     DSEQLRQDCDAL (SEQ ID NO: 8)
43-52     QEARERWNFD (SEQ ID NO: 9)
88-98     GGKRPSPSSAL (SEQ ID NO: 10)
101-110   GTSQEDHLDL (SEQ ID NO: 11)
119-129   RSPERPEGTPG (SEQ ID NO: 12)
135-145   QGRKRRQTSMT (SEQ ID NO: 13)

Human

MSEPAGDVRQ NPCGSKACRR LFGFVDSEQL SRDCDALMAG CIQEARERWN
FDFVTETPLE GDFAWERVRG LGLPKLYLPT GPRRGRDELG GGRRPGTSPA
LLQGTAEEDH VDLSLSCTLV PRSGEQAEGS PGGPGDSQGR KRRQTSMTDF
YHSKRRLIFS KRKP (SEQ ID NO: 2)

44-52 EARERWNFD (SEQ ID NO: 14)
79-87 PTGPRRGRD (SEQ ID NO: 15)
138-148 GRKRRQTSMT (SEQ ID NO: 16)

Mouse

MSNPGDVRPV PHRSKVCRCL FGPVDSEQLR RDCDALMAGC LQEARERWNF
DFVTETPLEG NFVWERVRSL GLPKVYLSPG SRSRDDLGGD KRPSTSSALL
QGPAPEDHVA LSLSCTLVSE RPEDSPGGPG TSQGRKRRQT SLTDFYHSKR
RLVFCKRKP (SEQ ID NO: 3)

24-34 VDSEQLRRDCD (SEQ ID NO: 17)
42-51 QEARERWNFD (SEQ ID NO: 18)
79-90 PGSRSRDDLGGD (SEQ ID NO: 19)
91-97 KRPSTSS (SEQ ID NO: 20)
119-130 SERPEDSPGGPG (SEQ ID NO: 21)
134-143 GRKRRQTSLT (SEQ ID NO: 22)

Rat

MSDPGDVRPV PHRSKVCRRL FGPVDSEQLS RDCDALMASC LQEARERWNF
DFATETPLEG NYVWERVRSP GLPKIYLSPG SRRRDDLGGD KRPSTSSALL
QGPGPAPEDH VALSLSCTLV (SEQ ID NO: 4)

52-59 QEARERWN (SEQ ID NO: 23)
81-87 SRRRDDL (SEQ ID NO: 24)
90-97 DKRPSTSS (SEQ ID NO: 25)

FIG. 7

Protein sequence used for prediction:

```
MSELSRDAHQIPRSSKACRCLFGPVDSEQLRQDCDALMASCVQEARERWN
FDFVTETPLEGDFAWERVRGLGLPKLYLPVGPRDDLGGGKRPSPSSALLQ
GTSQEDHLDLSLSCTLVTRSPERPEGTPGGPGPSQGRKRRQTSMTDFYHS
KRRLICSKRKP(SEQ ID NO: 1)
```

Epitope predicted inside protein below:

| Rank | Location | Epitope | Score | Recommend* |
|---|---|---|---|---|
| 1 | 27 - 46 | SEQLRQDCDALMASCVQEAR (SEQ ID NO: 26) | 1.000 | ⚑ |
| 2 | 134 - 153 | SQGRKRRQTSMTDFYHSKRR (SEQ ID NO: 27) | 0.735 | |

* The epitopes recommeneded are labeled by the flags

US 10,451,635 B2

```
                        SEQUENCE LISTING

<160> NUMBER OF SEQ ID NOS: 27

<210> SEQ ID NO 1
<211> LENGTH: 161
<212> TYPE: PRT
<213> ORGANISM: Bos taurus
<220> FEATURE:
<223> OTHER INFORMATION: p21 protein

<400> SEQUENCE: 1

Met Ser Glu Leu Ser Arg Asp Ala His Gln Ile Pro Arg Ser Lys
1               5                   10                  15

Ala Cys Arg Cys Leu Phe Gly Pro Val Asp Ser Glu Gln Leu Arg Gln
                20                  25                  30

Asp Cys Asp Ala Leu Met Ala Ser Cys Val Gln Glu Ala Arg Glu Arg
            35                  40                  45

Trp Asn Phe Asp Phe Val Thr Glu Thr Pro Leu Glu Gly Asp Phe Ala
        50                  55                  60

Trp Glu Arg Val Arg Gly Leu Gly Leu Pro Lys Leu Tyr Leu Pro Val
65                  70                  75                  80

Gly Pro Arg Asp Asp Leu Gly Gly Lys Arg Pro Ser Pro Ser Ser
                85                  90                  95

Ala Leu Leu Gln Gly Thr Ser Gln Glu Asp His Leu Asp Leu Ser Leu
            100                 105                 110

Ser Cys Thr Leu Val Thr Arg Ser Pro Glu Arg Pro Glu Gly Thr Pro
            115                 120                 125

Gly Gly Pro Gly Pro Ser Gln Gly Arg Lys Arg Gln Thr Ser Met
        130                 135                 140

Thr Asp Phe Tyr His Ser Lys Arg Arg Leu Ile Cys Ser Lys Arg Lys
145                 150                 155                 160

Pro

<210> SEQ ID NO 2
<211> LENGTH: 164
<212> TYPE: PRT
<213> ORGANISM: Homo sapiens
<220> FEATURE:
<223> OTHER INFORMATION: p21 protein

<400> SEQUENCE: 2

Met Ser Glu Pro Ala Gly Asp Val Arg Gln Asn Pro Cys Gly Ser Lys
1               5                   10                  15

Ala Cys Arg Arg Leu Phe Gly Pro Val Asp Ser Glu Gln Leu Ser Arg
                20                  25                  30

Asp Cys Asp Ala Leu Met Ala Gly Cys Ile Gln Glu Ala Arg Glu Arg
            35                  40                  45

Trp Asn Phe Asp Phe Val Thr Glu Thr Pro Leu Glu Gly Asp Phe Ala
        50                  55                  60

Trp Glu Arg Val Arg Gly Leu Gly Leu Pro Lys Leu Tyr Leu Pro Thr
65                  70                  75                  80

Gly Pro Arg Arg Gly Arg Asp Glu Leu Gly Gly Arg Arg Pro Gly
                85                  90                  95
```

```
Thr Ser Pro Ala Leu Leu Gln Gly Thr Ala Glu Asp His Val Asp
            100                 105                 110

Leu Ser Leu Ser Cys Thr Leu Val Pro Arg Ser Gly Glu Gln Ala Glu
        115                 120                 125

Gly Ser Pro Gly Gly Pro Gly Asp Ser Gln Gly Arg Lys Arg Arg Gln
    130                 135                 140

Thr Ser Met Thr Asp Phe Tyr His Ser Lys Arg Arg Leu Ile Phe Ser
145                 150                 155                 160

Lys Arg Lys Pro

<210> SEQ ID NO 3
<211> LENGTH: 159
<212> TYPE: PRT
<213> ORGANISM: Mus musculus
<220> FEATURE:
<223> OTHER INFORMATION: p21 protein

<400> SEQUENCE: 3

Met Ser Asn Pro Gly Asp Val Arg Pro Val Pro His Arg Ser Lys Val
1               5                   10                  15

Cys Arg Cys Leu Phe Gly Pro Val Asp Ser Glu Gln Leu Arg Arg Asp
            20                  25                  30

Cys Asp Ala Leu Met Ala Gly Cys Leu Gln Glu Ala Arg Glu Arg Trp
        35                  40                  45

Asn Phe Asp Phe Val Thr Glu Thr Pro Leu Glu Gly Asn Phe Val Trp
    50                  55                  60

Glu Arg Val Arg Ser Leu Gly Leu Pro Lys Val Tyr Leu Ser Pro Gly
65                  70                  75                  80

Ser Arg Ser Arg Asp Asp Leu Gly Gly Asp Lys Arg Pro Ser Thr Ser
                85                  90                  95

Ser Ala Leu Leu Gln Gly Pro Ala Pro Glu Asp His Val Ala Leu Ser
            100                 105                 110

Leu Ser Cys Thr Leu Val Ser Glu Arg Pro Glu Asp Ser Pro Gly Gly
        115                 120                 125

Pro Gly Thr Ser Gln Gly Arg Lys Arg Arg Gln Thr Ser Leu Thr Asp
    130                 135                 140

Phe Tyr His Ser Lys Arg Arg Leu Val Phe Cys Lys Arg Lys Pro
145                 150                 155

<210> SEQ ID NO 4
<211> LENGTH: 120
<212> TYPE: PRT
<213> ORGANISM: Rattus norvegicus
<220> FEATURE:
<223> OTHER INFORMATION: p21 protein

<400> SEQUENCE: 4

Met Ser Asp Pro Gly Asp Val Arg Pro Val Pro His Arg Ser Lys Val
1               5                   10                  15

Cys Arg Arg Leu Phe Gly Pro Val Asp Ser Glu Gln Leu Ser Arg Asp
            20                  25                  30

Cys Asp Ala Leu Met Ala Ser Cys Leu Gln Glu Ala Arg Glu Arg Trp
        35                  40                  45

Asn Phe Asp Phe Ala Thr Glu Thr Pro Leu Glu Gly Asn Tyr Val Trp
    50                  55                  60

Glu Arg Val Arg Ser Pro Gly Leu Pro Lys Ile Tyr Leu Ser Pro Gly
65                  70                  75                  80
```

-continued

Ser Arg Arg Arg Asp Asp Leu Gly Gly Asp Lys Arg Pro Ser Thr Ser
                85                  90                  95

Ser Ala Leu Leu Gln Gly Pro Gly Pro Ala Pro Glu Asp His Val Ala
            100                 105                 110

Leu Ser Leu Ser Cys Thr Leu Val
        115                 120

<210> SEQ ID NO 5
<211> LENGTH: 20
<212> TYPE: PRT
<213> ORGANISM: Bos taurus
<220> FEATURE:
<223> OTHER INFORMATION: p21 protein antigen

<400> SEQUENCE: 5

Ser Glu Gln Leu Arg Gln Asp Cys Asp Ala Leu Met Ala Ser Cys Val
1               5                   10                  15

Gln Glu Ala Arg
            20

<210> SEQ ID NO 6
<211> LENGTH: 129
<212> TYPE: PRT
<213> ORGANISM: Mus musculus
<220> FEATURE:
<221> NAME/KEY: MUTAGEN
<222> LOCATION: (7)..(7)
<223> OTHER INFORMATION: Xaa can be any naturally occurring amino acid.
      Heavy chain of anti-(bovine p21) antibody

<400> SEQUENCE: 6

Glu Val Gln Leu Val Gln Xaa Gly Ala Glu Val Lys Lys Pro Gly Glu
1               5                   10                  15

Ser Leu Arg Ile Ser Cys Lys Gly Ser Gly Asp Ser Phe Thr Thr Tyr
            20                  25                  30

Trp Ile Gly Trp Val Arg Gln Met Pro Gly Lys Gly Leu Glu Trp Met
        35                  40                  45

Gly Ile Ile Tyr Gly Gly Asp Ser Asp Thr Ile Tyr Glu Val Gln Leu
    50                  55                  60

Val Gln Gly Ala Glu Val Lys Lys Pro Gly Glu Ser Leu Ile Ser Cys
65                  70                  75                  80

Lys Gly Ser Gly Ser Phe Thr Tyr Trp Ile Gly Trp Val Arg Gln Met
                85                  90                  95

Pro Gly Lys Gly Leu Glu Trp Met Gly Ile Ile Tyr Gly Asp Ser Asp
            100                 105                 110

Thr Tyr Ser Pro Ser Phe Gln Gly Gln Val Thr Ile Ser Ala Asp Lys
        115                 120                 125

Ser

<210> SEQ ID NO 7
<211> LENGTH: 119
<212> TYPE: PRT
<213> ORGANISM: Mus musculus
<220> FEATURE:
<223> OTHER INFORMATION: Light chain of anti-(bovine p21) antibody

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Arg Trp
            20                  25                  30

```
Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Asp Ile Gln Met
 50                  55                  60

Thr Gln Ser Pro Ser Ser Leu Ser Ala Ser Val Gly Asp Arg Val Thr
 65                  70                  75                  80

Ile Thr Cys Arg Ala Ser Gln Gly Ile Ser Trp Leu Ala Trp Tyr Gln
                 85                  90                  95

Gln Lys Pro Glu Lys Ala Pro Lys Ser Leu Ile Tyr Ala Ala Ser Ser
            100                 105                 110

Leu Gln Ser Gly Val Pro Ser
            115

<210> SEQ ID NO 8
<211> LENGTH: 12
<212> TYPE: PRT
<213> ORGANISM: Bos taurus
<220> FEATURE:
<223> OTHER INFORMATION: amino acid residues 26 to 37 in p21 protein

<400> SEQUENCE: 8

Asp Ser Glu Gln Leu Arg Gln Asp Cys Asp Ala Leu
1               5                   10

<210> SEQ ID NO 9
<211> LENGTH: 10
<212> TYPE: PRT
<213> ORGANISM: Bos taurus
<220> FEATURE:
<223> OTHER INFORMATION: amino acid residues 43 to 52 in p21 protein

<400> SEQUENCE: 9

Gln Glu Ala Arg Glu Arg Trp Asn Phe Asp
1               5                   10

<210> SEQ ID NO 10
<211> LENGTH: 11
<212> TYPE: PRT
<213> ORGANISM: Bos taurus
<220> FEATURE:
<223> OTHER INFORMATION: amino acid residues 88 to 98 in p21 protein

<400> SEQUENCE: 10

Gly Gly Lys Arg Pro Ser Pro Ser Ser Ala Leu
1               5                   10

<210> SEQ ID NO 11
<211> LENGTH: 10
<212> TYPE: PRT
<213> ORGANISM: Bos taurus
<220> FEATURE:
<223> OTHER INFORMATION: amino acid residues 101 to 110 in p21 protein

<400> SEQUENCE: 11

Gly Thr Ser Gln Glu Asp His Leu Asp Leu
1               5                   10

<210> SEQ ID NO 12
<211> LENGTH: 11
<212> TYPE: PRT
<213> ORGANISM: Bos taurus
<220> FEATURE:
<223> OTHER INFORMATION: amino acid residues 119 to 129 in p21 protein
```

```
<400> SEQUENCE: 12

Arg Ser Pro Glu Arg Pro Glu Gly Thr Pro Gly
1               5                   10

<210> SEQ ID NO 13
<211> LENGTH: 11
<212> TYPE: PRT
<213> ORGANISM: Bos taurus
<220> FEATURE:
<223> OTHER INFORMATION: amino acid residues 135 to 145 in p21 protein

<400> SEQUENCE: 13

Gln Gly Arg Lys Arg Arg Gln Thr Ser Met Thr
1               5                   10

<210> SEQ ID NO 14
<211> LENGTH: 9
<212> TYPE: PRT
<213> ORGANISM: Homo sapiens
<220> FEATURE:
<223> OTHER INFORMATION: amino acid residues 44 to 52 in p21 protein

<400> SEQUENCE: 14

Glu Ala Arg Glu Arg Trp Asn Phe Asp
1               5

<210> SEQ ID NO 15
<211> LENGTH: 9
<212> TYPE: PRT
<213> ORGANISM: Homo sapiens
<220> FEATURE:
<223> OTHER INFORMATION: amino acid residues 79 to 87 in p21 protein

<400> SEQUENCE: 15

Pro Thr Gly Pro Arg Arg Gly Arg Asp
1               5

<210> SEQ ID NO 16
<211> LENGTH: 10
<212> TYPE: PRT
<213> ORGANISM: Homo sapiens
<220> FEATURE:
<223> OTHER INFORMATION: amino acid residues 138 to 148 in p21 protein

<400> SEQUENCE: 16

Gly Arg Lys Arg Arg Gln Thr Ser Met Thr
1               5                   10

<210> SEQ ID NO 17
<211> LENGTH: 11
<212> TYPE: PRT
<213> ORGANISM: Mus musculus
<220> FEATURE:
<223> OTHER INFORMATION: amino acid residues 24 to 34 in p21 protein

<400> SEQUENCE: 17

Val Asp Ser Glu Gln Leu Arg Arg Asp Cys Asp
1               5                   10

<210> SEQ ID NO 18
<211> LENGTH: 10
<212> TYPE: PRT
<213> ORGANISM: Mus musculus
<220> FEATURE:
<223> OTHER INFORMATION: amino acid residues 42 to 51 in p21 protein
```

-continued

<400> SEQUENCE: 18

Gln Glu Ala Arg Glu Arg Trp Asn Phe Asp
1               5                   10

<210> SEQ ID NO 19
<211> LENGTH: 12
<212> TYPE: PRT
<213> ORGANISM: Mus musculus
<220> FEATURE:
<223> OTHER INFORMATION: amino acid residues 79 to 90 in p21 protein

<400> SEQUENCE: 19

Pro Gly Ser Arg Ser Arg Asp Asp Leu Gly Gly Asp
1               5                   10

<210> SEQ ID NO 20
<211> LENGTH: 7
<212> TYPE: PRT
<213> ORGANISM: Mus musculus
<220> FEATURE:
<223> OTHER INFORMATION: amino acid residues 91 to 97 in p21 protein

<400> SEQUENCE: 20

Lys Arg Pro Ser Thr Ser Ser
1               5

<210> SEQ ID NO 21
<211> LENGTH: 12
<212> TYPE: PRT
<213> ORGANISM: Mus musculus
<220> FEATURE:
<223> OTHER INFORMATION: amino acid residues 119 to 130 in p21 protein

<400> SEQUENCE: 21

Ser Glu Arg Pro Glu Asp Ser Pro Gly Gly Pro Gly
1               5                   10

<210> SEQ ID NO 22
<211> LENGTH: 10
<212> TYPE: PRT
<213> ORGANISM: Mus musculus
<220> FEATURE:
<223> OTHER INFORMATION: amino acid residues 134 to 143 in p21 protein

<400> SEQUENCE: 22

Gly Arg Lys Arg Arg Gln Thr Ser Leu Thr
1               5                   10

<210> SEQ ID NO 23
<211> LENGTH: 8
<212> TYPE: PRT
<213> ORGANISM: Rattus norvegicus
<220> FEATURE:
<223> OTHER INFORMATION: amino acid residues 52 to 59 in p21 protein

<400> SEQUENCE: 23

Gln Glu Ala Arg Glu Arg Trp Asn
1               5

<210> SEQ ID NO 24
<211> LENGTH: 7
<212> TYPE: PRT
<213> ORGANISM: Rattus norvegicus
<220> FEATURE:
<223> OTHER INFORMATION: amino acid residues 81 to 87 in p21 protein

```
<400> SEQUENCE: 24

Ser Arg Arg Arg Asp Asp Leu
1               5

<210> SEQ ID NO 25
<211> LENGTH: 8
<212> TYPE: PRT
<213> ORGANISM: Rattus norvegicus
<220> FEATURE:
<223> OTHER INFORMATION: amino acid residues 90 to 97 in p21 protein

<400> SEQUENCE: 25

Asp Lys Arg Pro Ser Thr Ser Ser
1               5

<210> SEQ ID NO 26
<211> LENGTH: 20
<212> TYPE: PRT
<213> ORGANISM: Bos taurus
<220> FEATURE:
<223> OTHER INFORMATION: epitope in p21 protein

<400> SEQUENCE: 26

Ser Glu Gln Leu Arg Gln Asp Cys Asp Ala Leu Met Ala Ser Cys Val
1               5                   10                  15

Gln Glu Ala Arg
            20

<210> SEQ ID NO 27
<211> LENGTH: 20
<212> TYPE: PRT
<213> ORGANISM: Bos taurus
<220> FEATURE:
<223> OTHER INFORMATION: candidate epitope in p21 protein

<400> SEQUENCE: 27

Ser Gln Gly Arg Lys Arg Arg Gln Thr Ser Met Thr Asp Phe Tyr His
1               5                   10                  15

Ser Lys Arg Arg
            20
```

BEEF-SPECIFIC AGE DETERMINATION MARKER CONTAINING THE P21 PROTEIN

CROSS-REFERENCE TO RELATED APPLICATION

This patent application is a continuation-in-part of U.S. patent application Ser. No. 13/519,769 filed Jun. 28, 2012, which is a 371 National Stage of International Patent Application No. PCT/KR2010/009307, filed Dec. 24, 2010, which claims priority of Korean Patent Application No. 10-2009-0134212, filed Dec. 30, 2009, the entire contents of each of which are incorporated herein by reference.

BACKGROUND OF THE INVENTION

Field of the Invention

The present invention relates to a marker for determining the age of beef, comprising p21 protein specific for beef, an antibody specifically binding to bovine p21 protein, a beef-specific kit for determining the age of beef, comprising the antibody specifically binding to bovine p21 protein, and a method for determining beef age, comprising determining the age of beef, using an antigen-antibody binding reaction in which the muscle level of p21 protein is quantitatively analyzed with an antibody specific to bovine p21 protein.

Background Art

With the opening up of the domestic market to beef, South Korea imports a great deal of beef from Canada, the U.S. and other foreign countries. Of the beef imported from North America, such as Canada and the U.S., however, much is from cattle aged over 30 months, which is at great risk for bovine spongiform encephalopathy (BSE), evoking a national concern in South Korea. In fact, 95% of cattle with BSE are known to be over 30 months of age. It is thus required to import beef of less than 30 months of age. However, it is not easy to accurately determine the age of beef.

Currently, the age of beef is determined 1) by a birth certificate or estimated by 2) evaluating the ossification of the bones along the split vertebral column of the carcass or 3) counting the number of permanent incisor teeth in cattle at slaughter. Of these, the most reliable method is the determination made using a birth certificate. On American farms, however, the cattle are generally put out to pasture, so that their birthdays are not accurate. In fact, determining the age using the birth certificate is possible only in as few as 20% of the cattle imported from the U.S. Estimating the age by examining the ossification of the bones, that is, physiological skeletal maturity, is regarded as the most reliable among age determination methods with the naked eye, thus far, but the error rate is as large as about 15%. In addition, the number of teeth in cattle at slaughter is not scientifically accepted as an index for age estimation because the number of teeth greatly varies depending on breeding conditions. Particularly, the teeth-counting method is less accurate for cattle that are put out to pasture because they are not under regulated feeding conditions.

As stated above, currently used methods of determining the age of beef are not accurate, except for using the birth certificate.

Thanks to much study that has been done into determining the origin, grade and maturity of beef, Korean native and imported cattle carcasses can be classified in detail according to the origin, grade and maturity, but the exact age thereof cannot be determined. In addition, examining imported beef using currently used methods requires a great deal of time and expense because of the tremendous amount of such beef.

Therefore, there is a need for a scientific method for accurately determining the age of beef at low cost in a reduced period of time.

SUMMARY OF THE INVENTION

As the result of a study about a method of determining the age of slaughtered beef, the fact was verified that p21 protein is highly expressed in the muscle tissues of beef less than 30 months of age, whereas almost none of the protein is expressed in the muscle tissues of beef at the age of 30 months or more. According to the findings, an antibody specifically binding to bovine p21 was produced, thus completing the present invention.

Cumulating in the present invention, intensive and thorough research into accurately determining the age of beef, conducted by the present inventors, led to the finding that p21 protein is expressed at a high level in the muscle of cattle less than 30 months old, but almost not expressed in the muscles of cattle over 30 months of age.

TECHNICAL SOLUTION

It is another object of the present invention to provide a beef-specific marker for determining the age of beef, comprising p21 protein.

In addition, the present invention intends to provide an antibody specifically binding to p21 protein in the muscle tissues of beef.

It is another object of the present invention to provide a beef-specific kit for determining the age of beef, comprising an antibody specifically binding to bovine p21 protein.

It is a further object of the present invention to provide a method for determining the age of beef, using an antigen-antibody binding reaction in which the muscle level of p21 protein is quantitatively analyzed with an antibody specific to bovine p21 protein.

BRIEF DESCRIPTION OF THE DRAWINGS

FIG. 7 shows a region selected as an antigen peptide on bovine p21 amino acid sequence.

DETAILED DESCRIPTION OF THE INVENTION

Figure 1:
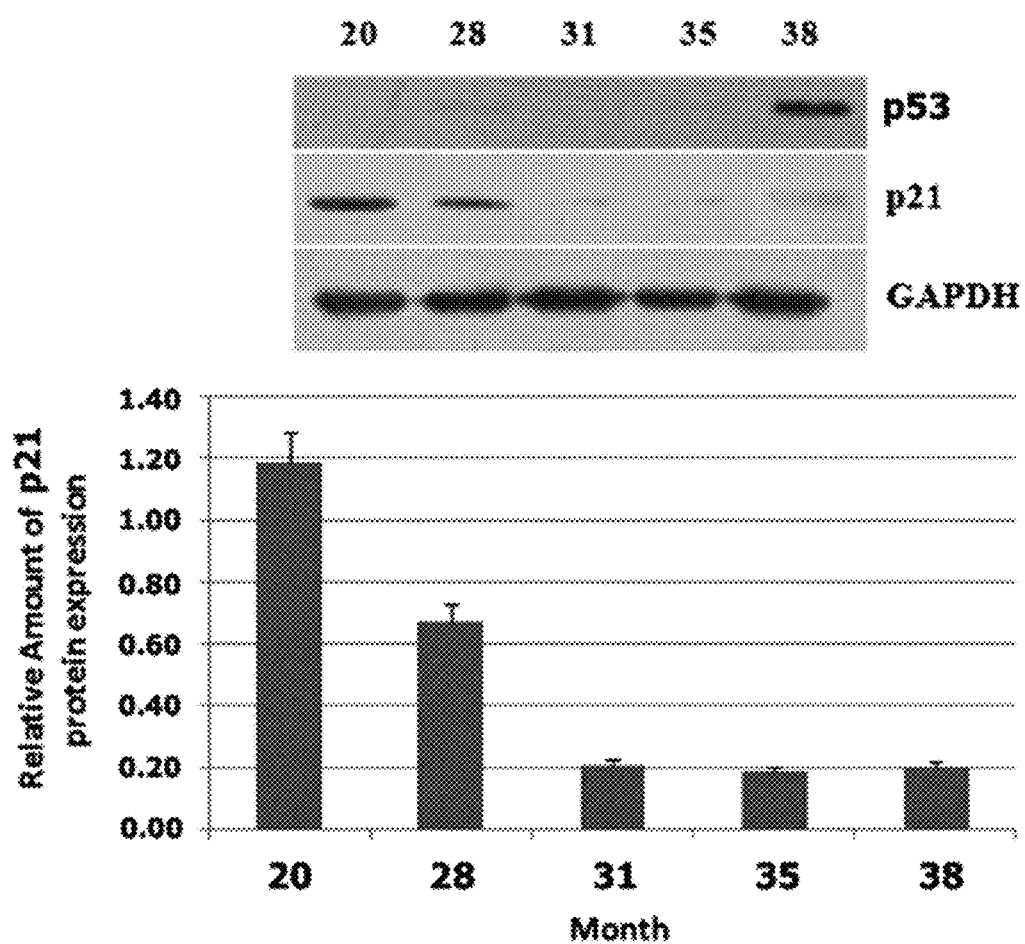
FIG. 1 shows expression levels of p53 and p21 in the muscle tissue of beef, as measured by Western blot.

In accordance with an aspect thereof, the present invention addresses a beef-specific marker for determining the age of beef, comprising p21 protein.

In addition, the present invention provides an antibody specifically binding to p21 protein in the muscle tissues of beef.

In accordance with another aspect thereof, the present invention addresses a beef-specific kit for determining the age of beef, comprising an antibody specifically binding to bovine p21 protein.

In accordance with a further aspect thereof, the present invention addresses a method for determining the age of beef, comprising detecting the muscle level of p21 protein by conducting an antigen-antibody binding reaction in which the p21 protein, useful as a beef specific marker, is reacted with an antibody specific to bovine p21 protein.

Below, a detailed description will be given of the present invention.

p21 protein is detected at a very high level in muscle tissues of cattle below 30 months of age, but almost no levels are found in muscle tissue of cattle over 30 months of age. In detail, beef is determined to be younger than 30 months when the expression level ratio of p21 to GAPDH is over 0.5 in the muscle tissue of beef while being older than 30 months of age in the muscle tissue of beef when the expression level ratio of p21 to GAPDH is below 0.5.

The expression of the p21 gene is tightly controlled by p53 because p21 is a transcriptional target of the tumor suppressor gene p53. p21, also known as CDK (cyclin-dependent kinase) inhibitor, functions as a regulator of cell cycle. The protein is encoded by the CDKN1A gene located on chromosome 6 (6p21.2) in humans. In the muscle tissue of cattle aged below 30 months, no p53 proteins are expressed. In contrast, a high expression level of p53 is detected in the muscle tissue of cattle aged over 30 months. In mice, further, expression levels of both p53 and p21 are found to increase with age. Therefore, p21 protein can be used as a beef-specific marker for the determination of age.

The beef-specific marker based on p21 protein in accordance with the present invention makes it easy to determine the age of beef, which is difficult to determine using conventional methods. Thus, it can be used as an index for cattle age. Further, the recruitment of the beef-specific marker in accordance with the present invention for the determination of age can significantly reduce the time and expense of performing a quarantine inspection on imported beef, and guarantee more reliable inspection, compared to conventional methods.

In addition, the antibody specifically binding to bovine p21 protein, according to the present invention, includes heavy chains composed of an amino acid sequence corresponding to SEQ ID NO: 6; and light chains composed of an amino acid sequence corresponding to SEQ ID NO: 7.

In addition, the beef-specific kit for determining the age of beef, according to the present invention, includes the antibody specifically binding to bovine p21 protein.

In one embodiment of the present invention, the beef-specific kit may comprise an antibody specifically binding to bovine p21 protein, a secondary antibody conjugate with a label that can react with a substrate to cause a chromatic change; a substrate solution which develops a color upon reaction with the label; a washing buffer and a reaction stop buffer.

The label conjugated to the secondary antibody is preferably a coloring agent which can bring about a color change as it reacts with its substrate. Representative among them are HRP (horseradish peroxidase), alkaline phosphatase, colloid gold, fluorescein such as FITC (poly L-lysine-fluorescein isothiocyanate) and RITC (rhodamine-B-isothiocyanate), and dye.

As for the substrate solution, it is dependent on the label. Examples include TMB (3,3',5,5'-tetramethyl bezidine), ABTS [2,2'-azino-bis(3-ethylbenzothiazoline-6-sulfonic acid)], and OPD (o-phenylenediamine). The coloring substrate is preferably provided in the form of a solution in buffer (0.1M NaOAc, pH 5.5).

The washing solution preferably contains phosphate buffer, NaCl and Tween 20. After the antibody is allowed to react with the antigen, the antigen-antibody complex is treated with the secondary antibody conjugate, followed by immobilization and then washing 3~6 times with the washing solution. A sulfuric acid solution may be used to stop the enzymatic reaction.

In one embodiment of the present invention, the age of beef can be determined using an antigen-antibody binding reaction in which the muscle level of p21 protein, useful as a beef-specific marker, is quantitatively analyzed with an antibody specific to bovine p21 protein. In greater detail, bovine p21 protein is separated by SDS-PAGE, transferred and fixed onto an immobilizer which is then treated with an antibody against bovine p21 protein to form an antigen-antibody complex which is useful for determining the expression level of bovine p21 protein. That is, the age of beef can be judged to be below 30 months when the relative expression level of bovine p21 protein to GAPDH in the muscle tissue is over 0.5 and to be over 30 months when the relative expression level is below 0.5.

As the immobilizer useful in the antigen-antibody binding reaction, a nitrocellulose membrane, a PVDF (polyvinylidene difluoride) membrane, a 96-well plate formed of polyvinyl resin or polystyrene resin, or a slide glass may be used.

The antigen-antibody binding reaction may be assayed using a typical method such as enzyme-linked immunosorbent assay (ELISA), radioimmunoassay (RIA), sandwich assay, reverse-transcription polymerase chain reaction (RT-PCR), realtime PCR, Western blot, immunoprecipitation, immunohistochemical staining, tandem mass spectrometry (LC-MS/MS), immunofluorescence assay, enzyme-substrate coloring assay, antigen-antibody aggregation.

EXAMPLES

A better understanding of the present invention may be obtained through the following examples which are set forth to illustrate, but are not to be construed as limiting the present invention.

Example 1

Determination of Beef Age—Western Blot

Three cattle per group of naturally aged 20, 28, 31, 35 and 38 month old cattle were used. They were slaughtered and their beef muscle tissues were analyzed for protein level with respect to age. In more detail, the beef muscle tissues were homogenized in buffer [20 mM Tris-HCl, PIC (protease inhibitor cocktail, Roche)], left for 30 min on ice, and centrifuged for min at 12,000 rpm at 4° C. The protein level of the supernatant thus obtained was determined by the BCL method. The same protein amounts were mixed with 5×SDS sample buffer [60 mM Tris-Cl (pH 6.8), 25% glycerol, 2% SDS, 14.4 mM β-mercaptoethanol, 0.1% bromophenol blue] and boiled for 5 min. The proteins thus denatured (30~40 μg) were run on 12% polyacrylamide gel by electrophoresis and then transferred onto a nitrocellulose membrane. In this regard, electrophoresis was performed on a 0.2 μm nitrocellulose membrane in transfer buffer [25 mM Tris-base (pH 8.3), 192 mM glycine, 20% methanol] for 2 hours under an electric field of 1 A. Thereafter, the nitrocellulose membrane was stained with Ponceau to determine protein positions. The membrane was blocked for one hour with 5% skimmed milk in TTBS (Tris Buffered Saline with Tween 20), followed by incubation with a dilution of primary antibodies (p21, p53) at room temperature for 2 hours or at 4° C. overnight. Then, the membrane was washed three times for 5 min with TBS-0.1% Tween 20 before incubation with a 1:2000 dilution of HRP-conjugated goat anti-mouse IgG or HRP-conjugated rabbit anti-goat IgG in TBS containing 5% skimmed milk at room temperature for one hour. Again, the membrane was rinsed three times for 5 min with TBS-0.1% Tween 20, after which an ECL kit (Pierce) containing a peroxidase substrate was used to develop the proteins on an X-ray film (Kodak). Also, relative expression levels of p21 (to GAPDH) were quantitatively analyzed using a densitometer.

The results are shown in FIG. 1.

As can be seen in FIG. 1, protein p53 was expressed in the muscle tissues of beef only from cattle aged 38 months whereas almost no p21 protein was found in cattle over 30 months of age. In addition, the relative expression level of p21 to GAPDH was found to be greater than 0.5 in the muscle tissues of cattle below 30 months of age, and to be below 0.5 in the muscle tissues of cattle over 30 months of age. Therefore, p21 protein can be used as a beef-specific marker for determining the age of cattle.

Comparative Example 1

Determination of Mouse Age—Western Blot

C57BL/6 mice were bred in an SPF (specific pathogen free) facility for up to 24 months. A selection was made of mice aged 3, 6, 9, 12, 15, 18, 21, and 24 months. After no clear diseases were found in appearance and anatomically from the mice, organs were excised therefrom. Dermal tissues with a dimension of about 1 cm×1 cm were frozen in liquid nitrogen and milled in a mortar. The milled dermal tissues were dissolved in RIPA buffer [5 mM Tris-Cl (pH 7.4), 1% NP-40, 0.25% sodium deoxycholate, 150 mM NaCl, 1 mM EDTA] by ultrasonication. Two rounds of centrifugation at 14,000×g for 10 min separated proteins in a supernatant. SDS-PAGE was performed with 20 mg of the proteins thus obtained. As a secondary antibody, an anti-mouse antibody (Amersham, Chicago, Ill.) was diluted 1:10,000 before incubation with the proteins. Color development was achieved using ECL (enhanced chemiluminescence system; Amersham).

Figure 2:
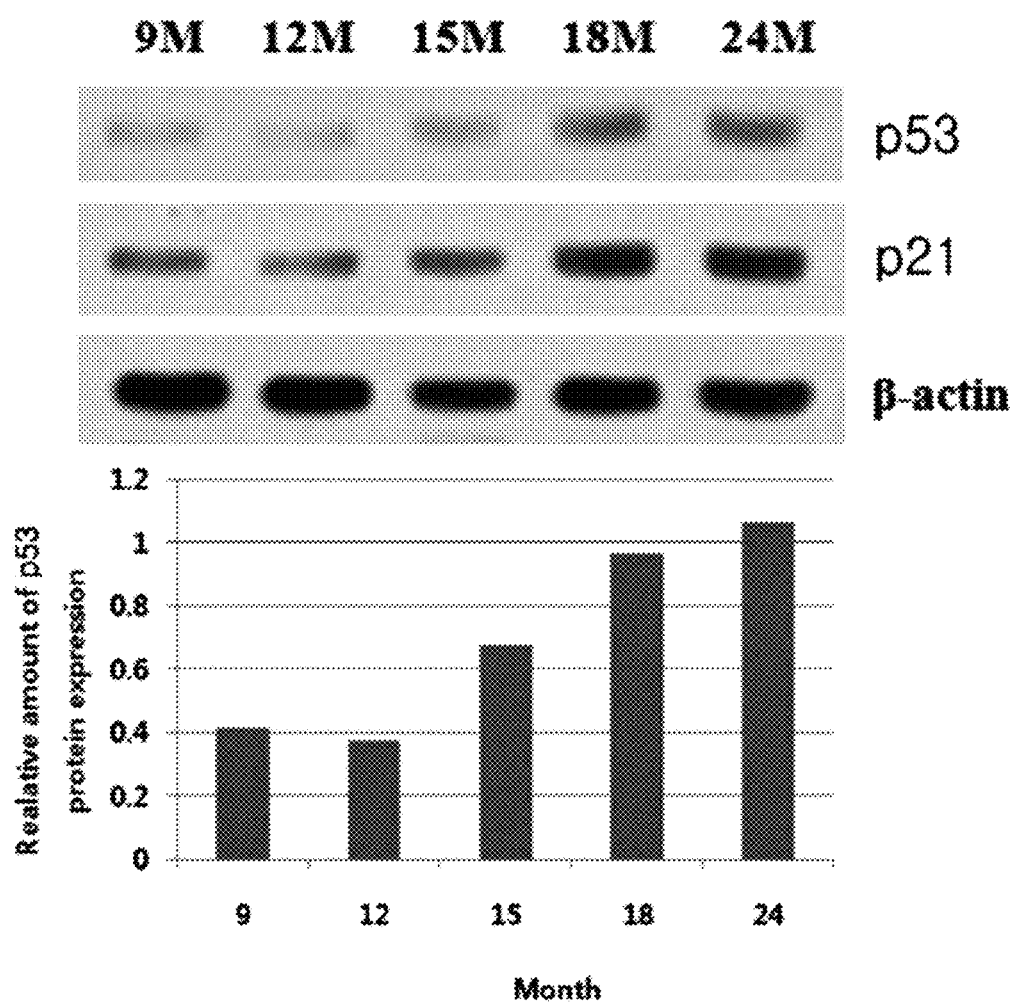
FIG. 2 shows expression levels of p53 and p21 in the dermal tissue of mice, as measured by Western blot.
Figure 3:
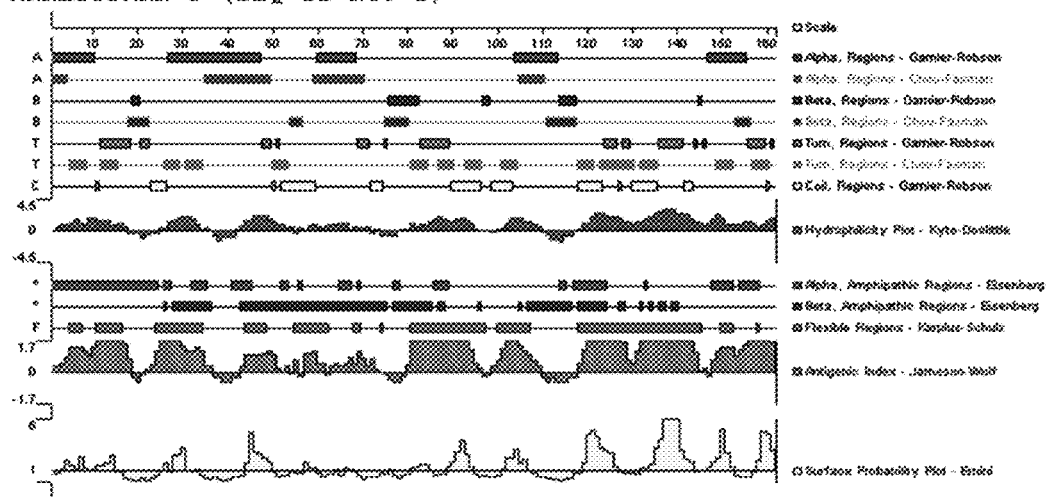
FIGS. 3 to 6 show the results of amino acid sequence analysis of bovine, human, mouse, and rat p21 proteins, respectively, for evaluating the antigenicity of p21 proteins from different species.
Figure 4:
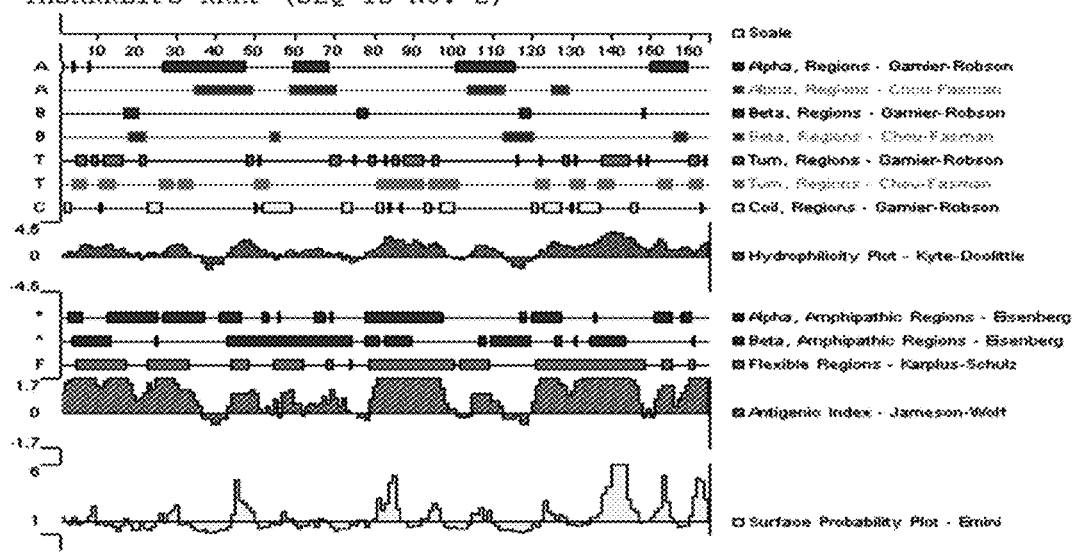
Figure 5:
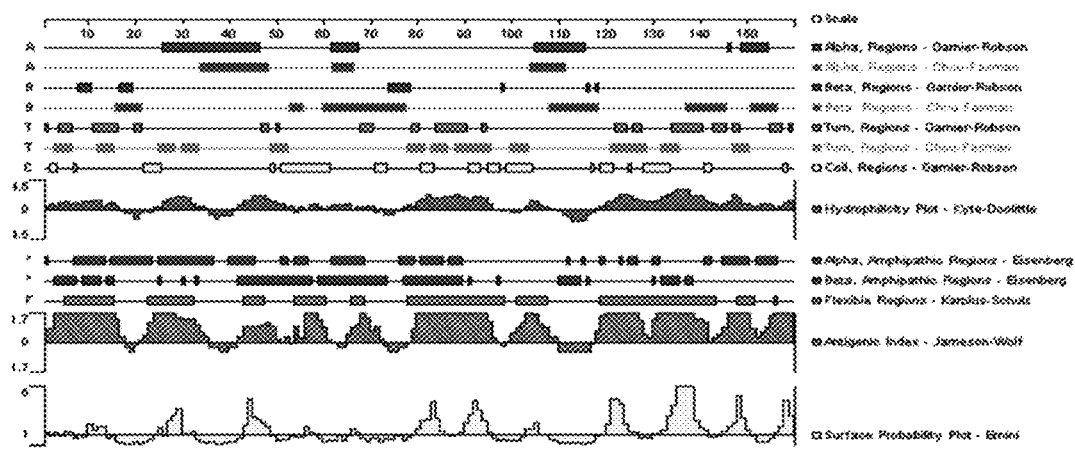
Figure 6:
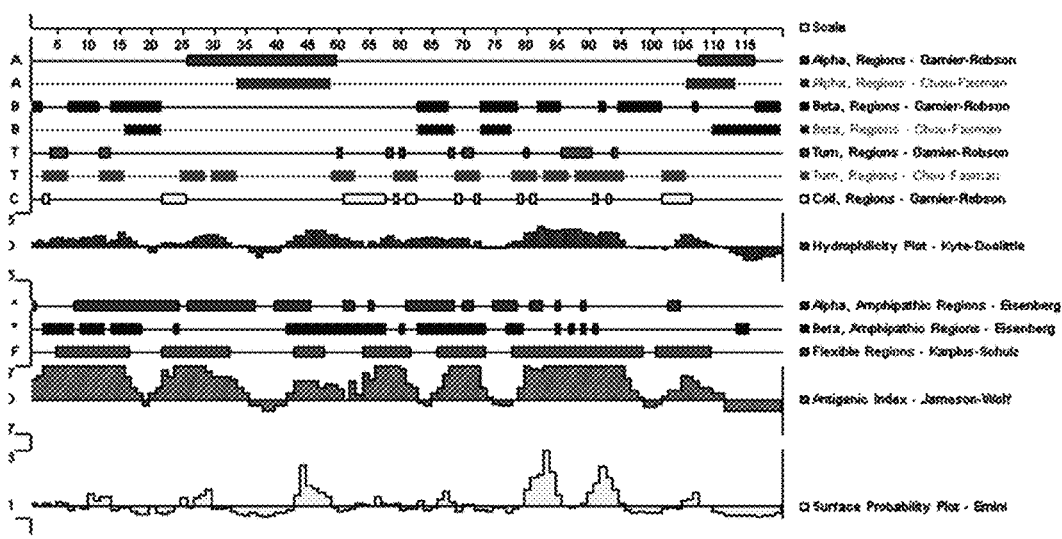

The results are shown in FIG. 2.

As can be seen in FIG. 2, the expression levels of p53 and p21 in the dermal tissue of mice were found to increase with age.

Example 2

Production of an Antibody Specifically Binding to Bovine p21 Protein 2-1. Selection of an Antigen Peptide As illustrated in FIGS. 3 to 6, for producing an antibody specifically binding to bovine p21 protein, analysis of amino acid sequences of p21 proteins was performed by aligning amino acid sequences of bovine, human, mouse, and rat p21 proteins. Information about amino acid sequences of bovine, human, mouse, and rat p21 proteins was obtained from NCBI, a publicly known database, and the amino acid sequences of bovine, human, mouse, and rat p21 proteins were represented as sequence numbers 1 to 4 in order (FIGS. 3 to 6).

As the result of performing antigenicity evaluation of the sequence numbers 1 to 4, an amino acid sequence (SEQL-RQDCDALMASCVQEAR, SEQ ID NO: 5) corresponding to a region between amino acids 27 to 46 of bovine p21 protein, which is the region responsible for clearly discriminating the difference of p21 proteins between species, was selected as the antigen peptide (FIG. 7).

2-2. Production of an Antibody Against p21 Protein

The selected antigen peptide, SEQ ID NO: 5, was attached with keyhole limpet hemocyanin (KLH; MW: 5,000,000) to facilitate immune response and then used in production of the antibody.

0.01 to 0.1 mg of the KLH-attached antigen peptide together with complete Freund's adjuvant (CFA) was administrated to 5 mice (BALB/c/10W) for producing an antibody through a subcutaneous injection (SC) or an intraperitoneal injection (IP) to induce immune response, and after 10 days, 0.01 to 0.1 mg of the antigen peptide together with incomplete Freund's adjuvant (IFA) was subcutaneously or intraperitoneally injected, i.e., adjuvant:antigen (1:1 or 1:2 by volume), as a secondary immunization to activate immune response one more time.

At 10 days after the secondary immunization, 0.01 to 0.1 mg of the antigen peptide together with IFA was subcutaneously or intraperitoneally injected again to finally induce the activation of third immune response.

At 5 to 14 days after the third immunization, the mice were sacrificed, and subsequently whole blood of mice was harvested, followed by separation of serum therefrom. Immunity for the antigen was determined in the separated serum using ELISA assay.

2-3. ELISA Assay

The antigen peptide (SEQ ID NO: 5) selected in Example 2-1 was incubated at 37° C. for 1 hour and then coated on the wells of a culture plate, and then the antigen-containing solution was discarded, followed by washing two times to remove unbound antigens.

Mouse serum and BSA were diluted with PBS to be 100 μg/ml, respectively. In an experiment using ELISA, 3 strips, wherein each of strips is composed of the antigen-coated 8 wells, were used for each experimental group, and 100 μl of the diluted mice serum or BSA solution was added to each strip according to concentrations shown in Table 1 below.

TABLE 1

|   |   | A | B | C | D | E | F | G | H |
|---|---|---|---|---|---|---|---|---|---|
| 1 | MOUSE SERUM g/ml | 100 | 50 | 25 | 12.5 | 6.25 | 3.12 | 1.56 | 0.78 |

TABLE 1-continued

| | | A | B | C | D | E | F | G | H |
|---|---|---|---|---|---|---|---|---|---|
| 2 | MOUSE SERUM g/ml | 100 | 50 | 25 | 12.5 | 6.25 | 3.12 | 1.56 | 0.78 |
| 3 | BSA g/ml | 100 | 100 | 0 | 0 | 100 | 100 | 0 | 0 |

Subsequently, 250 µl of blocking solution was added into the wells and then incubated at 37° C. for 1 hour, followed by discarding of the blocking solution and washing two times with PBS. The antigen-coated wells treated with the blocking solution were incubated at 37° C. for 1 hour with 100 µl of each of antibodies properly diluted with the blocking solution, wherein the kinds of antibodies and a method of antibody treating are as follows:

In the case of HRP-conjugated goat anti-mouse IgG antibody, the antibody solution was added into the entire wells of the first row and A, B, C, and D wells of the third row; and, In the case of HRP-conjugated goat anti-mouse IgM antibody, the antibody solution was added into the entire wells of the second row and E, F, G, and H wells of the third row.

Figure 8:
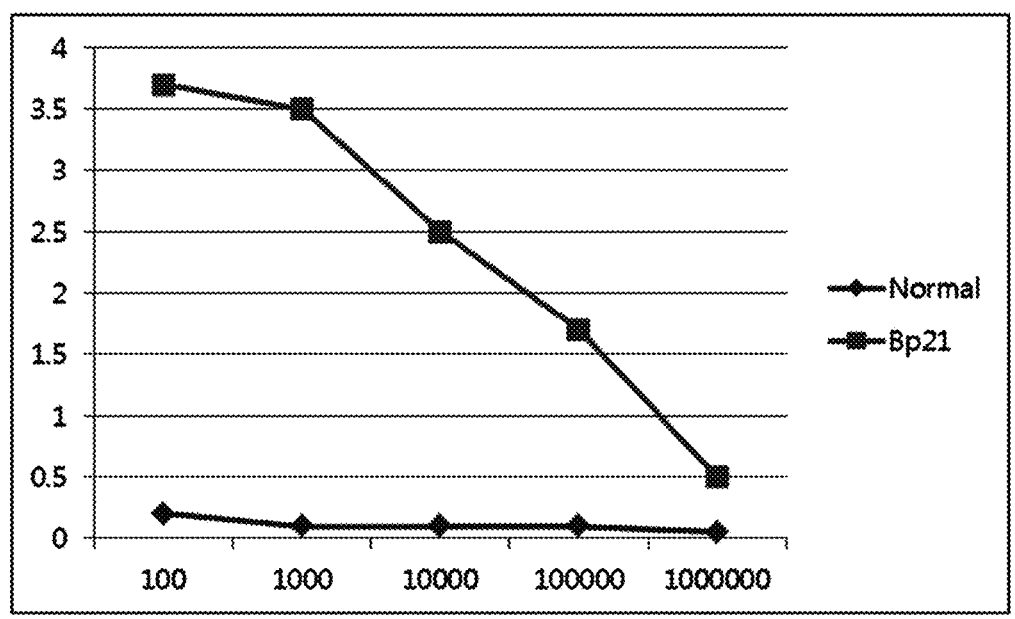
FIG. 8 shows the result of ELISA of serum collected from mice which were twice subcutaneously or intraperitoneally injected with an antigen peptide, i.e., SEQ ID NO: 5, and then subjected to final third immune response.

Subsequently, the antibody-treated wells were washed with 200 µl of washing solution 3 times. After washing, 100 µl of substrate reaction solution was added into each well and then incubated at 37° C. for 30 minutes to induce color change, followed by measurement of absorbance at 450 nm using an ELISA reader. As the result of the ELISA analysis, as illustrated in FIG. 8, the antibody produced in Example 2-2 was verified to bind to the antigen peptide (SEQ ID NO: 5) with the sensitivity of 1/10,000 dilution.

IgG was purified from the serum of the immunized mice using a protein G column, and only the antibody with affinity for the antigen was separated and purified.

2-5. Investigation of an Effect of the Anti-p21 Antibody

To confirm whether the produced antibody specifically binds to bovine p21 protein, the anti-p21 antibody of the present invention was compared to a commercially available antibody (p21 antibody (C-19): sc-397, Santa Cruz Biotechnology, Inc.) using western blot. The protein samples of the western blot are as follows:

Control: muscle tissues from a mouse;
Bovine: muscle tissues from a bovine at 18 months of age;
Mouse: muscle tissues from a mouse at 18 months of age; and
Human: fibroblasts at passage 20.

Certain amounts of the protein samples were subjected to SDS-polyacrylamide gel electrophoresis (SDS-PAGE) and then transferred on a nitrocellulose membrane (Amersham Biosciences, Inc.). Subsequently, the blotted membrane was incubated in 1% BSA-TBST for 1 to 2 hours or in 5% nonfat dry milk for 30 minutes, followed by 15 minutes of washing two times. The membrane was incubated with a primary antibody for 1 to 2 hours. After the primary antibody reaction, the membrane was washed for 15 minutes two times and then incubated with a horseradish peroxidase-linked secondary antibody for 1 hour, followed by washing. After finishing the antibody reaction, the membrane was treated with developing solution for 1 to 2 minutes and subsequently subjected to an X-ray exposure.

Figure 9:
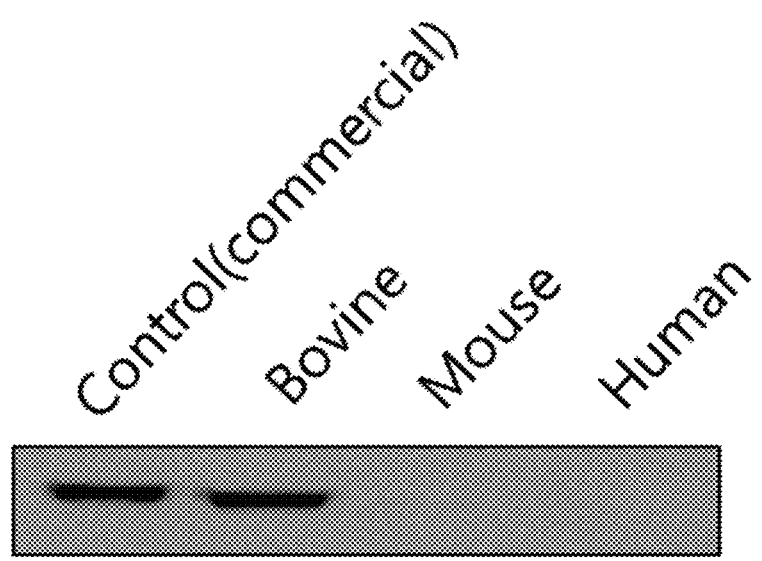
FIG. 9 shows a western blot result verifying a specific interaction between bovine p21 protein and an anti-p21 antibody of the present invention.

As a result, as illustrated in FIG. 9, the anti-p21 antibody of the present invention was verified to specifically bind only to bovine p21 protein.

Example 3

Analysis of Amino Acid Sequence of the Anti-p21 Antibody

Amino acid sequence of the produced antibody was analyzed using a mass spectrometer, and amino acid sequences of the heavy and light chains of the antibody are shown in Table 2 below.

TABLE 2

| | Amino acid sequence |
|---|---|
| Heavy chain | EVQLVQXGAEVKKPGESLRISCKGSGDSFTTYWIGWVRQMP GKGLEWMGIIYGGDSDTIYEVQLVQGAEVKKPGESLISCKG SGSFTYWIGWVRQMPGKGLEWMGIIYGDSDTYSPSFQGQVT ISADKS (SEQ ID NO: 6) |
| Light chain | DIQMTQSPSSLSASVGDRVTITCRASQGISRWLAWYQQKPE KAPKSLIYAASSLQSGVPSDIQMTQSPSSLSASVGDRVTIT CRASQGISWLAWYQQKPEKAPKSLIYAASSLQSGVPS (SEQ ID NO: 7) |

Example 4

Determination of Age of Beef Using the Anti-p21 Antibody

Using the same method introduced in Example 1, the relationship between p21 expression and the ages of naturally aged bovines, including 20, 28, 31, 35, and 38 month old bovines, was analyzed using the anti-p21 antibody according to Example 2.

Figure 10:
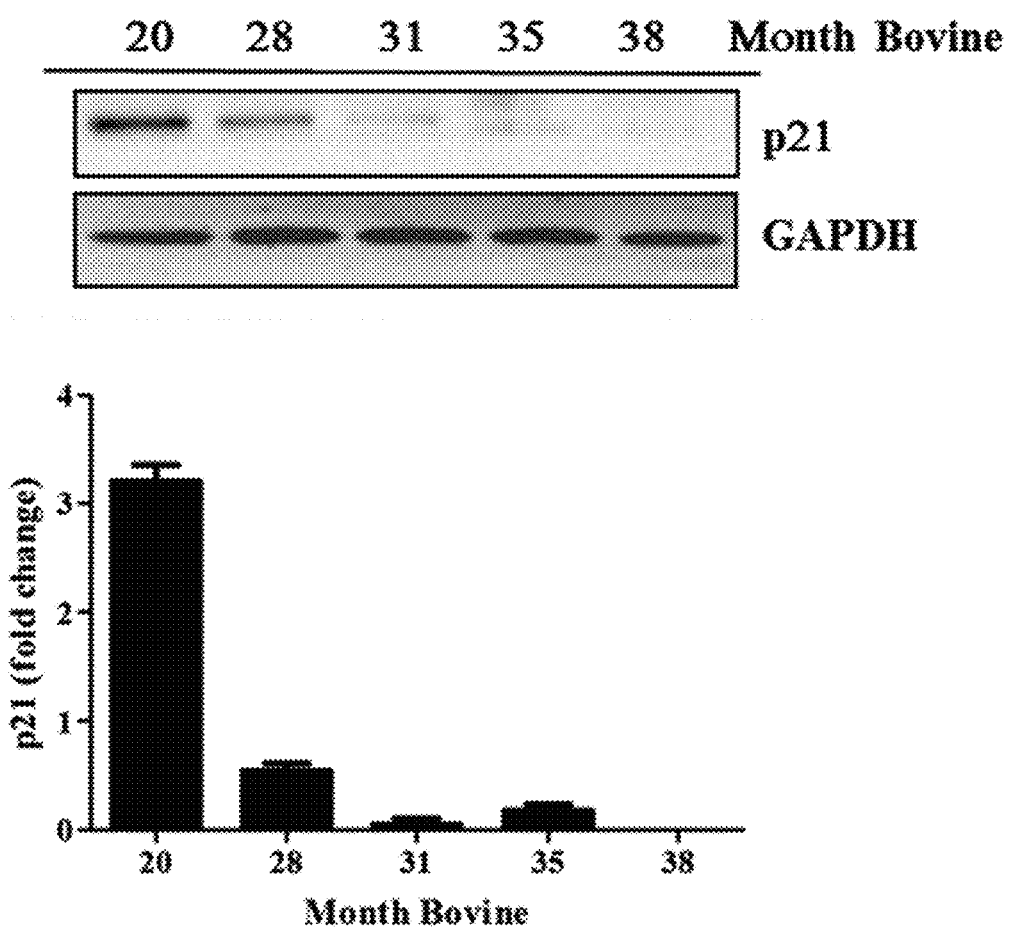
FIG. 10 shows a result determining the age of beef using an anti-p21 antibody of the present invention.

The relative expression levels of p21 proteins corresponding to the bovine samples were quantified, based on the expression level of GAPDH. As illustrated in FIG. 10, the relative expression amounts of p21 proteins were 0.5 or more in the muscle tissues of bovines at the age of less than 30 months, whereas, in the muscle tissues of bovines at the age of 30 months or more, the relative expression amounts of p21 proteins were less than 0.5.

According to the results, it was verified that the age of beef may be easily and exactly determined using the anti-p21 antibody of the present invention.

INDUSTRIAL APPLICABILITY

Because p21 protein is expressed at a high level in the muscle tissue of cattle below 30 months of age, but not at all in the muscle tissue of cattle over 30 months of age, as described hitherto, the p21 protein can be used as a beef-specific marker for the determination of age of beef. The antibody specifically binding to bovine p21 protein in accordance with the present invention makes it easy to determine the age of beef, which is difficult to determine using conventional methods, and beef-specific marker based on p21 protein can be used as an index for cattle age. Further, the recruitment of the antibody in accordance with the present invention for the determination of age can significantly reduce the time and expense that is taken up by performing a quarantine inspection on imported beef, and guarantee more reliable inspection, compared to conventional methods.

We claim:

1. An antibody specifically binding to bovine p21 (cyclin-dependent kinase inhibitor 1), comprising a heavy chain consisting of SEQ ID NO: 6; and a light chain consisting of SEQ ID NO: 7.

2. A method for determining the age of beef muscle tissue, comprising:
   (a) obtaining a sample of beef muscle tissue for which an estimated age is needed;
   (b) measuring an expression level of p21 protein in the sample of beef muscle tissue by carrying out an antigen-antibody binding reaction using the antibody of claim 1, followed by an antigen-antibody binding reaction in which a secondary antibody specifically binds to the antibody of claim 1;
   (c) measuring an expression level of GAPDH (glyceraldehyde 3-phosphate dehydrogenase) in the sample of beef muscle tissue by carrying out an antigen-antibody binding reaction in which an anti-GAPDH primary antibody specifically binds to protein GAPDH, followed by an antigen-antibody binding reaction in which a secondary antibody specifically binds to the anti-GAPDH primary antibody; and
   (d) determining the age of the sample of beef muscle tissue to be less than 30 months when an expression level ratio of p21 to GAPDH in the sample of beef muscle tissue is greater than 0.5, and over 30 months when the expression level ratio of p21 to GAPDH in the sample of beef muscle tissue is below 0.5;
   wherein each of the secondary antibodies used in steps (b) and (c) are selected from the group consisting of HRP-conjugated goat anti-mouse IgG and HRP-conjugated rabbit anti-goat IgG and anti-mouse antibody.

3. The method according to claim 2, wherein the measuring steps (b) and (c) are performed using a method selected from the group consisting of enzyme-linked immunosorbent assay (ELISA), radioimmunoassay (RIA), sandwich assay, Western blot, immunoprecipitation, immunohistochemical staining, tandem mass spectrometry (LC-MS/MS), immunofluorescence assay, enzyme-substrate coloring assay, antigen-antibody aggregation, and a combination thereof.

4. A beef-specific age determination kit, comprising an antibody of claim 1.

* * * * *